United States Patent
Sakaguchi et al.

(10) Patent No.: US 8,680,305 B2
(45) Date of Patent: Mar. 25, 2014

(54) METHOD FOR OBTAINING POLYUNSATURATED FATTY ACID DERIVATIVES

(75) Inventors: Hiroyuki Sakaguchi, Fuchu (JP); Hideaki Kobayashi, Fuchu (JP); Yoshihisa Misawa, Akaiwa (JP); Keisuke Uryu, Akaiwa (JP); Yoshio Shimizu, Akaiwa (JP)

(73) Assignees: Q.P. Corporation, Tokyo (JP); Bizen Chemical Co., Ltd., Okayama (JP)

( * ) Notice: Subject to any disclaimer, the term of this patent is extended or adjusted under 35 U.S.C. 154(b) by 205 days.

(21) Appl. No.: 13/062,969

(22) PCT Filed: Sep. 2, 2009

(86) PCT No.: PCT/JP2009/004311
§ 371 (c)(1),
(2), (4) Date: May 27, 2011

(87) PCT Pub. No.: WO2010/029706
PCT Pub. Date: Mar. 18, 2010

(65) Prior Publication Data
US 2011/0224452 A1    Sep. 15, 2011

(30) Foreign Application Priority Data
Sep. 10, 2008    (JP) .................................. 2008-231773

(51) Int. Cl.
*C11B 7/00*    (2006.01)
(52) U.S. Cl.
USPC ........... 554/193; 554/191; 554/194; 554/196; 554/175; 554/74
(58) Field of Classification Search
None
See application file for complete search history.

(56) References Cited

U.S. PATENT DOCUMENTS

| | | | |
|---|---|---|---|
| 4,277,412 A | 7/1981 | Logan | |
| 5,189,189 A * | 2/1993 | Misawa et al. | 554/194 |
| 5,777,141 A * | 7/1998 | Brunner et al. | 554/175 |
| 6,313,330 B1 | 11/2001 | Kiyohara et al. | |

FOREIGN PATENT DOCUMENTS

| | | |
|---|---|---|
| EP | 0 576 191 A2 | 12/1993 |
| EP | 1 065 196 A1 | 1/2001 |
| JP | 4-126798 A | 4/1992 |
| JP | 4-154896 A | 5/1992 |
| JP | 4-159398 A | 6/1992 |
| JP | 4-218596 A | 8/1992 |
| JP | 4-243849 A | 8/1992 |
| JP | 2000-44983 A | 2/2000 |
| JP | 2001-240893 A | 9/2001 |
| JP | 2001-335794 A | 12/2001 |
| JP | 2006-241245 A | 9/2006 |
| JP | 4078383 B1 | 4/2008 |

OTHER PUBLICATIONS

International Preliminary Report on Patentability and Written Opinion mailed Apr. 28, 2011, in PCT International Application No. PCT/JP2009/004311.
International Search Report, dated Oct. 20, 2009 issued in PCT/JP2009/004311.
Japanese Office Action for Japanese Application No. 2008-231773, dated Aug. 13, 2013.
Extended European Search Report, dated Sep. 17, 2013, for European Application No. 09812855.6.

* cited by examiner

*Primary Examiner* — Yate K Cutliff
(74) *Attorney, Agent, or Firm* — Birch, Stewart, Kolasch & Birch, LLP

(57) ABSTRACT

A method of obtaining a polyunsaturated fatty acid derivative comprises contacting a mixture of fatty acid derivatives with a silver salt aqueous solution, and adjusting the free fatty acid content in the silver salt aqueous solution to 0.2 meq or less per gram of silver when repeatedly using the silver salt aqueous solution. A polyunsaturated fatty acid derivative having high purity and excellent quality can thus be economically obtained.

5 Claims, No Drawings ise cost. Therefore, technology that makes it possible to repeatedly recycle a silver salt aqueous solution over a long period has been desired to inexpensively provide a polyunsaturated fatty acid and derivatives thereof having excellent quality.

METHOD FOR OBTAINING POLYUNSATURATED FATTY ACID DERIVATIVES

TECHNICAL FIELD

The present invention relates to a method of inexpensively obtaining a polyunsaturated fatty acid derivative having excellent quality suitable for drugs, cosmetic preparations, food, and the like.

BACKGROUND ART

A polyunsaturated fatty acid and derivatives thereof have many physiological activities such as reducing the fat level in blood, and have been used as a raw material for drugs, cosmetic preparations, food, and the like for many years. Methods of purifying a polyunsaturated fatty acid and derivatives thereof having high purity and excellent quality have been studied.

For example, a silver complex-forming technique has been known (Patent Documents 1 to 4). The silver complex-forming technique utilizes a property in which a polyunsaturated fatty acid and derivatives thereof become water-soluble as a result of forming a complex with a silver ion. Patent Documents 1 to 4 disclose that a silver salt that has been used to purify a polyunsaturated fatty acid and derivatives thereof can be recycled. However, a silver salt very easily deteriorates. When a polyunsaturated fatty acid and derivatives thereof are purified using a silver salt that has deteriorated, an excellent purified product cannot be obtained because impurities may be mixed, or a deterioration in flavor may occur. Therefore, the reality was that it was very difficult to recycle a silver salt. When industrially purifying a polyunsaturated fatty acid and derivatives thereof, it was necessary to prepare a new silver salt aqueous solution for each purification process. This significantly increases the purification cost. Therefore, technology that makes it possible to repeatedly recycle a silver salt aqueous solution over a long period has been desired to inexpensively provide a polyunsaturated fatty acid and derivatives thereof having excellent quality.

RELATED-ART DOCUMENT

Patent Document

Patent Document 1: Japanese Patent No. 2786748
Patent Document 2: Japanese Patent No. 2895258
Patent Document 3: Japanese Patent No. 2935555
Patent Document 4: Japanese Patent No. 3001954

DISCLOSURE OF THE INVENTION

Problems to be Solved by the Invention

An object of the present invention is to provide polyunsaturated fatty acid derivative inexpensively by improving the recycling efficiency of silver salt aqueous solution in the silver complex-forming technique.

Means for Solving the Problems

The inventors of the present invention conducted extensive studies on a method of obtaining a polyunsaturated fatty acid derivative using a silver salt aqueous solution. Surprisingly, the inventors found that a polyunsaturated fatty acid derivative having excellent quality can be obtained while repeatedly recycling a silver salt aqueous solution by adjusting the free fatty acid content in the silver salt aqueous solution to be recycled to be equal to or less than a given value. This finding has led to the completion of the present invention. The inventors also found that a polyunsaturated fatty acid derivative having more excellent quality can be obtained by adjusting the acid value of a mixture of fatty acid derivatives that is contacted with the silver salt aqueous solution to be equal to or less than a given value.

Specifically, the present invention provides the following.
(1) A method of obtaining a polyunsaturated fatty acid derivative comprising contacting a mixture of fatty acid derivatives including a polyunsaturated fatty acid derivative with a silver salt aqueous solution to obtain the polyunsaturated fatty acid derivative, and adjusting the free fatty acid content in the silver salt aqueous solution to 0.2 meq or less per gram of silver when repeatedly using the silver salt aqueous solution.
(2) The method according to (1), wherein the free fatty acid content is adjusted to 0.2 meq or less per gram of silver by contacting the silver salt aqueous solution with an adsorbent.
(3) The method according to (1) or (2), wherein the mixture of fatty acid derivatives before being contacted with the silver salt aqueous solution has an acid value of 5 or less.
(4) The method according to any one of (1) to (3), wherein the acid value of the mixture of fatty acid derivatives before being contacted with the silver salt aqueous solution is adjusted to 5 or less by contacting the mixture with an adsorbent.

Effects of the Invention

The above method of obtaining a polyunsaturated fatty acid derivative makes it possible to industrially recycle the silver salt aqueous solution used for the silver complex-forming technique. Accordingly, a polyunsaturated fatty acid derivative having excellent quality can be inexpensively obtained.

DESCRIPTION OF EXEMPLARY EMBODIMENTS

A method of obtaining a polyunsaturated fatty acid derivative according to one embodiment of the present invention is described in detail below. Note that the unit "%" used herein refers to "mass %".

The method of obtaining a polyunsaturated fatty acid derivative according to one embodiment of the present invention includes the steps of: contacting a mixture of fatty acid derivatives with a silver salt aqueous solution, and adjusting the free fatty acid content in the silver salt aqueous solution to 0.2 meq or less per gram of silver when repeatedly using the silver salt aqueous solution. This makes it possible to recycle the silver salt aqueous solution used for the above method (silver complex-forming technique). Accordingly, a polyunsaturated fatty acid derivative having excellent quality can be obtained even when recycling the silver salt aqueous solution.

More specifically, the method according to one embodiment of the present invention includes the steps of contacting a mixture of fatty acid derivatives that differ in the number of carbon atoms and/or the degree of unsaturation with a silver salt aqueous solution to form a water-soluble complex of a polyunsaturated fatty acid derivative, removing fatty acid derivatives other than the polyunsaturated fatty acid derivative that do not faun a complex, dissociating the polyunsaturated fatty acid derivative from the complex to obtain the polyunsaturated fatty acid derivative, and adjusting the free fatty acid content in the silver salt aqueous solution to 0.2 meq or less per gram of silver when repeatedly using the silver salt aqueous solution.

The term "polyunsaturated fatty acid" used herein refers to an unsaturated fatty acid that has 16 or more carbon atoms and includes two or more double bonds in the molecule. Examples of the polyunsaturated fatty acid include docosahexaenoic acid (C22:6, DHA), eicosapentaenoic acid (C20:5, EPA), arachidonic acid (C20:4, AA), docosapentaenoic acid (C22:5, DPA), stearidonic acid (C18:4), linolenic acid (C18:3), linoleic acid (C18:2), and the like. The polyunsaturated fatty acid derivative obtained by the method according to the present invention refers to a derivative which is not a free fatty acid. Examples of the polyunsaturated fatty acid derivative include ester-type derivatives (e.g., methyl ester and ethyl esters), amide-type derivatives (e.g., amide and methylamide), fatty alcohol-type derivatives, triglycerides, diglycerides, monoglycerides, and the like of polyunsaturated fatty acids.

The silver salt used for the method according to the present invention is not particularly limited insofar as the silver salt forms a complex with an unsaturated bond in an unsaturated fatty acid. Examples of the silver salt include silver nitrate, silver perchlorate, silver acetate, silver trichloroacetate, silver trifluoroacetate, and the like. The silver salt is preferably dissolved in water at a concentration of 15% or more, more preferably 20% or more, and still more preferably 40% or more to prepare a silver salt aqueous solution which is used for obtaining the polyunsaturated fatty acid derivative. The upper limit of the silver salt concentration in the silver salt aqueous solution may be the saturation concentration.

The free fatty acid content in the silver salt aqueous solution can be calculated by the principle of the modified Duncombe method (Duncombe W. G: Clin. Chem. Acta., 9, 122-125, 1964). Specifically, a copper test solution is added to a sample to obtain a salt fanned from a free fatty acid in the sample and copper. The salt is isolated using an extractant. A color reagent including bathocuproine is then added to produce a chelate compound of copper and bathocuproine (yellow-orange). The yellow-orange absorbance is then measured to determine concentration of the free fatty acid in the sample.

In the method according to the present invention, the collected silver salt aqueous solution may be contacted with an adsorbent to adjust the free fatty acid content to 0.2 meq or less per gram of silver before recycling the silver salt aqueous solution. Examples of the adsorbent include activated carbon, activated alumina, activated clay, acid clay, silica gel, diatomaceous earth, aluminium oxide, magnesium oxide, and the like. These adsorbents may be used either individually or in combination.

The silver salt aqueous solution can be contacted with the adsorbent by an arbitrary method. For example, the silver salt aqueous solution may be contacted with the adsorbent by adding the adsorbent to the silver salt aqueous solution, and stirring the mixture, or passing the silver salt aqueous solution through a column packed with the adsorbent.

The free fatty acid content in the collected silver salt aqueous solution may be adjusted to 0.2 meq or less per gram of silver before recycling the silver salt aqueous solution by dilution, concentration adjustment or extraction with an organic solvent. The concentration of the collected silver salt aqueous solution may be adjusted by evaporating water (heating under reduced pressure), or appropriately adding a silver salt or water while measuring the specific gravity.

The free fatty acid content in the silver salt aqueous solution to be recycled is 0.2 meq or less per gram of silver, preferably 0.18 meq or less per gram of silver, and more preferably 0.12 meq or less per gram of silver, so as to obtain the resulting polyunsaturated fatty acid derivative having a preferable flavor and acid value.

In the method according to the present invention, it is preferable to adjust the acid value of the mixture of fatty acid derivatives to 5 or less before contacting the mixture with the silver salt aqueous solution. This suppresses an increase in the free fatty acid content in the silver salt aqueous solution subjected to the above process. Accordingly, the free fatty acid content in the silver salt aqueous solution can be easily adjusted to 0.2 meq or less per gram of silver. This makes it possible to efficiently recycle the silver salt aqueous solution.

In the method according to the present invention, the acid value of the mixture of fatty acid derivatives may be adjusted to 5 or less before contacting the mixture with the silver salt aqueous solution by contacting the mixture with the an adsorbent. Examples of the adsorbent include activated carbon, activated alumina, activated clay, acid clay, silica gel, diatomaceous earth, aluminium oxide, magnesium oxide, and the like. These adsorbents may be used either individually or in combination.

The mixture of fatty acid derivatives may be contacted with the adsorbent by an arbitrary method. For example, the mixture of fatty acid derivatives can be contacted with the adsorbent by adding the adsorbent to the mixture, and stirring the mixture, or passing the mixture through a column packed with the adsorbent.

The acid value of the mixture of fatty acid derivatives may be adjusted to 5 or less by distillation before contacting the mixture with the silver salt aqueous solution.

In the method according to one embodiment of the present invention, the polyunsaturated fatty acid derivative may be selectively separated from the mixture of fatty acid derivatives by adding an aqueous solution of a silver salt that forms a complex with an unsaturated bond to the mixture of fatty acid derivatives including the polyunsaturated fatty acid derivative, stirring the mixture preferably for 5 minutes to 4 hours (more preferably 10 minutes to 2 hours) to form a water-soluble complex of the silver salt and the polyunsaturated fatty acid derivative, and selectively dissolving only the polyunsaturated fatty acid derivative in the silver salt aqueous solution.

The lower limit of the reaction temperature of the polyunsaturated fatty acid derivative and the silver salt aqueous solution is determined so that the silver salt aqueous solution can be in a liquid state. The upper limit of the reaction temperature is 100° C. The reaction temperature is preferably 10 to 30° C. taking account of the oxidation stability of the polyunsaturated fatty acid derivative, the solubility of the silver salt in water, the complex production rate, and the like.

It is preferable to contact the polyunsaturated fatty acid derivative with the silver salt aqueous solution in an inert gas atmosphere (e.g., nitrogen atmosphere) under light-blocking condition, taking account of the oxidation stability of the polyunsaturated fatty acid derivative and the stability of the silver salt.

The polyunsaturated fatty acid derivative may be dissociated from the complex of the polyunsaturated fatty acid derivative and the silver salt by an arbitrary method. For example, the polyunsaturated fatty acid derivative may be dissociated from the complex by extraction with an organic solvent, or by insolubilizing and separating the polyunsaturated fatty acid derivative by adding water.

The method of obtaining a polyunsaturated fatty acid derivative according to one embodiment of the present invention is further described below by way of examples and the like. Note that the present invention is not limited to the following examples.

EXAMPLES

<Measurement of Free Fatty Acid>
1. Preparation of Standard Solution
(1) 0.114 g of myristic acid was accurately weighed into a 100 ml measuring flask, and filled up with dimethyl sulfoxide to obtain 100 ml solution.
(2) 1.5 g of triethanolamine was added to another 100 ml measuring flask, and filled up with purified water to obtain 100 ml solution.
(3) 0.10 g of tetrasodium ethylenediaminetetraacetate tetrahydrate was added to still another 100 ml measuring flask, and filled up with purified water to obtain 100 ml solution.
(4) 20 ml of the solution obtained by (1), 10 ml of the solution obtained by (2), and 10 ml of the solution obtained by (3) were exactly measured in volume into a 100 ml measuring flask, and filled up with purified water to obtain 100 ml of a standard solution.
2. Preparation of Copper Test Solution
(1) 6.49 g of copper (II) sulfate pentahydrate and 20.0 g of sodium chloride were added to a beaker, and dissolved in purified water. The solution was added to a 100 ml measuring flask, mixed with a wash liquid of the beaker, and filled up with purified water to obtain 100 ml solution.
(2) 14.9 g of triethanolamine was added to another 100 ml measuring flask, and filled up with purified water to obtain 100 ml solution.
(3) The solutions obtained by (1) and (2) were mixed in equal amounts (volume ratio) to obtain a copper test solution.
3. Preparation of Color Reagent
0.189 g of bathocuproine was added to a 250 ml measuring flask, and filled up with 2-butanol to obtain 250 ml solution.
4. Procedure
(1) 5 µl of the silver salt aqueous solution and 500 µl of the standard solution were respectively added to test tubes provided with a cap, followed by the addition of 1 ml of the copper test solution.
(2) 3 ml of a chloroform/heptane mixture (1:1, volume ratio) was added to each test tube. After capping each test tube, each test tube was vigorously shaken with the hand for three minutes.
(3) After uncapping each test tube, the mixture was centrifuged (3000 rpm).
(4) 2 ml of the supernatant liquid was collected, and added to another test tube. After adding 2 ml of the color reagent, the mixture was lightly shaken up.
(5) After 2 to 3 minutes, the absorbance at 475 nm was measured using purified water as a control.
5. Calculation Expression
The free fatty acid concentration in the silver salt aqueous solution was calculated by the following expression (1).

$$\text{Free fatty acid concentration (meq/L)} = B/A \times D/C \quad (1)$$

A: Absorbance when using the standard solution
B: Absorbance when using the test solution
C: Amount (µl) of sample
D: Amount (µl) of standard solution The free fatty acid content per gram of silver was calculated by the following expressions (2) and (3).

Silver concentration (g/L) in the used silver salt=concentration (%) of the used silver salt/ 100×specific gravity of the used silver salt× atomic weight of silver in the used silver salt/ molecular weight of the used silver salt (2)

Free fatty acid content (meq/g) per gram of silver=free fatty acid concentration (meq/L)/silver concentration (g/L) in the used silver salt (3)

Example 1

A polyunsaturated fatty acid ethyl ester was obtained from a mixture of fatty acid ethyl esters by the following method.

350 kg of distilled water was added to 350 kg of silver nitrate. The mixture was stirred to obtain a silver nitrate aqueous solution. After adding 154 kg of a mixture of fatty acid ethyl esters (acid value: 0.08, POV: 3.3, EPA ethyl ester concentration: 45.6%, DHA ethyl ester concentration: 3.8%) to the silver nitrate aqueous solution (700 kg), the mixture was stirred at 10° C. for 20 minutes. The mixture was then allowed to stand for 1 hour until the mixture was separated into two phases. The lower layer was then isolated. After adding 1000 kg of water to the isolated product, this mixture was stirred at 60° C. for 20 minutes. The mixture was then allowed to stand for 1 hour until the mixture was separated into two phases. The upper layer was isolated to obtain a concentrate of a polyunsaturated fatty acid ethyl ester. Separately, the lower layer containing silver nitrate was collected, and the free fatty acid content was measured. The lower layer containing silver nitrate was concentrated, adjusted in concentration, and again used to purify a polyunsaturated fatty acid ethyl ester. The above operations were repeated to treat 14 batches of the mixture.

The results are shown in Table 1. The free fatty acid content in the silver nitrate aqueous solution during recycling was 0.2 meq or less per gram of silver. The product thus obtained (EPA ethyl ester concentration: 81 to 84%) had a satisfactory POV, acid value, and quality such as flavor

TABLE 1

| | Silver salt | | | | Polyunsaturated fatty acid derivative obtained | | |
|---|---|---|---|---|---|---|---|
| Batch No. | Free fatty acid content (meq/g) | POV (meq/kg) | Acid value | Flavor | Yield (%) | EPA ethyl ester (%) | DHA ethyl ester (%) |
| 1 | 0.065 | 3.2 | 0.15 | Good | 74.1 | 83.4 | 8.5 |
| 2 | 0.064 | 3.5 | 0.26 | Good | 72.6 | 83.1 | 8.2 |
| 3 | 0.074 | 4.5 | 0.34 | Good | 70.5 | 83.3 | 8.2 |
| 4 | 0.080 | 5.1 | 0.24 | Good | 64.1 | 83.0 | 8.3 |
| 5 | 0.089 | 3.4 | 0.38 | Good | 72.2 | 81.8 | 10.0 |
| 6 | 0.089 | 3.6 | 0.32 | Good | 68.3 | 82.9 | 8.8 |
| 7 | 0.087 | 3.9 | 0.12 | Good | 68.0 | 82.8 | 9.0 |
| 8 | 0.077 | 3.3 | 0.26 | Good | 65.8 | 82.7 | 9.1 |
| 9 | 0.095 | 2.0 | 0.34 | Good | 68.7 | 80.8 | 11.4 |
| 10 | 0.104 | 3.0 | 0.45 | Good | 65.2 | 81.7 | 10.0 |
| 11 | 0.105 | 2.4 | 0.47 | Good | 61.0 | 81.9 | 10.0 |
| 12 | 0.114 | 1.5 | 0.31 | Good | 62.7 | 81.8 | 10.0 |
| 13 | 0.114 | 1.7 | 0.44 | Good | 61.9 | 81.6 | 10.0 |
| 14 | 0.118 | 1.3 | 0.36 | Good | 61.8 | 81.6 | 10.1 |

Example 2

A polyunsaturated fatty acid ethyl ester was obtained from a mixture of fatty acid ethyl esters by the following method.

350 kg of distilled water was added to 350 kg of silver nitrate. The mixture was stirred to obtain a silver nitrate aqueous solution. After adding 150 kg of a mixture of fatty acid ethyl esters (acid value: 5.98, POV: 2.1, EPA ethyl ester concentration: 44.3%, DPA ethyl ester concentration: 5.1%) to the silver nitrate aqueous solution (700 kg), the mixture was stirred at 10° C. for 20 minutes. The mixture was then allowed to stand for 1 hour until the mixture was separated into two phases. The lower layer was then isolated. After adding 1000 L of water to the isolated product, this mixture was stirred at 60° C. for 20 minutes. The mixture was then allowed to stand for 1 hour until the mixture was separated into two phases. The upper layer was isolated to obtain a concentrate of a polyunsaturated fatty acid ethyl ester. Separately, the lower layer containing silver nitrate was collected. After adding aluminium oxide in an amount equal to 10% of the amount of the lower layer, the mixture was stirred at 60°

C. for 20 minutes. Aluminium oxide was then removed by filtration. The free fatty acid content in the lower layer subjected to the aluminium oxide treatment was measured. The lower layer subjected to the aluminium oxide treatment was concentrated, adjusted in concentration, and again used to obtain a polyunsaturated fatty acid ethyl ester. The above operations were repeated to treat 10 batches of the mixture. The results are shown in Table 2. The product thus obtained (EPA ethyl ester concentration: 80 to 84%) had a satisfactory POV, acid value, and quality such as flavor.

TABLE 2

| Batch No. | Silver salt Free fatty acid content (meq/g) | POV (meq/kg) | Acid value | Flavor | Polyunsaturated fatty acid derivative obtained | | |
|---|---|---|---|---|---|---|---|
| | | | | | Yield (%) | EPA ethyl ester (%) | DHA ethyl ester (%) |
| 1 | 0.001 | 2.2 | 0.04 | Good | 93.1 | 80.2 | 11.1 |
| 2 | 0.001 | 1.9 | 0.08 | Good | 91.3 | 81.4 | 10.8 |
| 3 | 0.001 | 2.3 | 0.07 | Good | 92.6 | 82.4 | 9.9 |
| 4 | 0.002 | 2.8 | 0.10 | Good | 90.2 | 83.5 | 9.1 |
| 5 | 0.004 | 2.9 | 0.11 | Good | 91.6 | 80.8 | 11.3 |
| 6 | 0.004 | 2.8 | 0.09 | Good | 90.8 | 81.7 | 10.9 |
| 7 | 0.003 | 2.5 | 0.11 | Good | 89.8 | 82.1 | 9.5 |
| 8 | 0.005 | 2.2 | 0.10 | Good | 89.1 | 81.1 | 10.2 |
| 9 | 0.005 | 2.0 | 0.14 | Good | 90.6 | 80.7 | 9.4 |
| 10 | 0.007 | 1.8 | 0.11 | Good | 90.3 | 81.3 | 10.3 |

Example 3

A polyunsaturated fatty acid methyl ester was obtained from a mixture of fatty acid methyl esters by the following method.

350 kg of distilled water was added to 350 kg of silver nitrate. The mixture was stirred to obtain a silver nitrate aqueous solution. After adding 150 kg of a mixture of fatty acid methyl esters (acid value: 6.74, POV: 2.3, EPA methyl ester concentration: 46.2%, DPA methyl ester concentration: 3.6%) to the silver nitrate aqueous solution (700 kg), the mixture was stirred at 10° C. for 20 minutes. The mixture was then allowed to stand for 1 hour until the mixture was separated into two phases. The lower layer was then isolated. After adding of 900 L of cyclohexane to the isolated product, this mixture was stirred at 50° C. for 20 minutes. The mixture was then allowed to stand for 1 hour until the mixture was separated into two phases. The upper layer was isolated to obtain a concentrate of a polyunsaturated fatty acid methyl ester. Separately, the lower layer containing silver nitrate was collected. After adding aluminium oxide in an amount equal to 10% of the amount of the lower layer, the mixture was stirred at 60° C. for 20 minutes. Aluminium oxide was then removed by filtration. The free fatty acid content in the lower layer subjected to the aluminium oxide treatment was measured. The lower layer subjected to the aluminium oxide treatment was adjusted in concentration, and again used to obtain a polyunsaturated fatty acid methyl ester. The above operations were repeated to treat 10 batches of the mixture. The results are shown in Table 3. The product thus obtained (EPA methyl ester concentration: 84 to 89%) had a satisfactory POV, acid value, and quality such as flavor.

TABLE 3

| Batch No. | Silver salt Free fatty acid content (meq/g) | POV (meq/kg) | Acid value | Flavor | Polyunsaturated fatty acid derivative obtained | | |
|---|---|---|---|---|---|---|---|
| | | | | | Yield (%) | EPA methyl ester (%) | DPA methyl ester (%) |
| 1 | 0.001 | 2.2 | 0.02 | Good | 96.8 | 86.9 | 8.1 |
| 2 | 0.001 | 2.7 | 0.02 | Good | 95.3 | 84.4 | 7.9 |
| 3 | 0.001 | 1.7 | 0.04 | Good | 97.4 | 88.1 | 7.6 |
| 4 | 0.001 | 3.0 | 0.06 | Good | 93.3 | 87.7 | 6.8 |
| 5 | 0.002 | 1.4 | 0.05 | Good | 98.1 | 85.6 | 6.9 |
| 6 | 0.002 | 1.8 | 0.06 | Good | 94.2 | 86.3 | 6.4 |
| 7 | 0.002 | 2.5 | 0.09 | Good | 97.8 | 88.3 | 6.3 |
| 8 | 0.003 | 2.4 | 0.10 | Good | 92.5 | 87.0 | 5.5 |
| 9 | 0.003 | 2.8 | 0.13 | Slight fishy odor | 93.8 | 83.8 | 6.6 |
| 10 | 0.004 | 2.3 | 0.14 | Slight fishy odor | 96.6 | 89.0 | 5.3 |

Example 4

A polyunsaturated fatty acid ethyl ester was obtained by treating 40 batches of a mixture of fatty acid ethyl esters by the following method.

350 kg of distilled water was added to 350 kg of silver nitrate. The mixture was stirred to obtain a silver nitrate aqueous solution. After mixing 150 kg of a mixture of fatty acid ethyl esters (40 batches, acid value: 0.05 to 4.11, POV: 2.2 to 3.5, EPA ethyl ester concentration: 41.1 to 58.1%, DHA ethyl ester concentration: 3.9 to 8.7%) with the silver nitrate aqueous solution (700 kg), the mixture was stirred at 10° C. for 20 minutes. The mixture was then allowed to stand for 1 hour until the mixture was separated into two phases. The lower layer was then isolated. After adding 1000 kg of water to the isolated product, this mixture was stirred at 60° C. for 20 minutes. The mixture was then allowed to stand for 1 hour until the mixture was separated into two phases. The upper layer was isolated to obtain a concentrate of a polyunsaturated fatty acid ethyl ester. Separately, the lower layer containing silver nitrate was collected, and the free fatty acid content was measured. The lower layer containing silver nitrate was concentrated, adjusted in concentration, appropriately subjected to an activated carbon treatment when the free fatty acid content in the silver nitrate aqueous solution had approached 0.2 meq per gram of silver, and again used to purify a polyunsaturated fatty acid ethyl ester. The activated carbon treatment was performed by adding activated carbon in an amount equal to 10% of the amount of the silver nitrate aqueous solution, stirring the mixture at 60° C. for 20 minutes, and filtering the mixture. The silver nitrate aqueous solution subjected to the activated carbon treatment was again used to obtain a polyunsaturated fatty acid ethyl ester. The above operations were repeated. The results are shown in Table 4. The product (EPA ethyl ester concentration: 75 to 84%) obtained using the silver nitrate aqueous solution for which the free fatty acid content was appropriately reduced by the activated carbon treatment had a satisfactory POV, acid value, and quality such as flavor.

The free fatty acid content per gram of silver increased in the 15th and 16th batches (acid value of mixture of fatty acid ethyl esters: 4.11) as compared with 1st to 14th batches (acid value of mixture of fatty acid ethyl esters: 0.05 to 1.22). It was thus confirmed that the free fatty acid content in the silver salt after obtaining a polyunsaturated fatty acid ethyl ester can be kept at a low value by decreasing the acid value of the fatty acid derivatives that are contacted with the silver salt aqueous solution, so as to facilitate recycling of the silver salt aqueous solution.

TABLE 4

| Batch No. | Silver salt Acid value of fatty acid derivative | Free fatty acid content (meq/g) | POV (meq/g) | Acid value | Flavor | Yield (%) | EPA ethyl ester (%) | DHA ethyl ester (%) |
|---|---|---|---|---|---|---|---|---|
| 1 | 1.22 | 0.029 | 4.4 | 0.05 | Good | 73.7 | 76.7 | 13.7 |
| 5 |  | 0.038 | 2.8 | 0.09 | Good | 74.4 | 77.5 | 13.5 |
| 10 |  | 0.068 | 2.5 | 0.16 | Good | 73.2 | 78.8 | 13.2 |
| 12 | 0.05 | 0.066 | 3.3 | 0.16 | Good | 69.7 | 78.4 | 14.3 |
| 15 | 4.11 | 0.139 | 3.0 | 1.13 | Slight fishy odor | 75.6 | 76.2 | 15.9 |
| 16 |  | 0.166 | 5.7 | 1.27 | Slight fishy odor | 75.5 | 76.5 | 16.0 |
| Activated carbon treatment on silver nitrate aqueous solution | | | | | | | | |
| 17 | 1.49 | 0.039 | 3.0 | 0.15 | Good | 77.8 | 74.7 | 18.5 |
| 20 | 0.32 | 0.049 | 2.5 | 0.16 | Good | 73.8 | 84.9 | 7.5 |
| 25 | 1.09 | 0.129 | 4.0 | 0.96 | Slight fishy odor | 75.1 | 80.0 | 15.6 |
| 30 | 0.07 | 0.170 | 3.4 | 1.29 | Slight fishy odor | 9.4 | 83.8 | 9.1 |
| Activated carbon treatment on silver nitrate aqueous solution | | | | | | | | |
| 31 | 2.69 | 0.006 | 4.2 | 0.04 | Good | 81.1 | 83.7 | 8.3 |
| 35 | 3.27 | 0.087 | 4.8 | 0.52 | Good | 82.6 | 82.5 | 9.7 |
| 40 |  | 0.181 | 5.9 | 1.09 | Slight fishy odor | 76.7 | 82.3 | 9.6 |

Example 5

A polyunsaturated fatty acid ethyl ester was obtained from a mixture of fatty acid ethyl esters by the following method.

300 kg of aluminium oxide was added to 2000 kg of a mixture of fatty acid ethyl esters (acid value: 7.32, POV: 2.3, EPA ethyl ester concentration: 42.3%, DHA ethyl ester concentration: 1.6%). The mixture was stirred for 1 hour. After removing aluminium oxide by filtration, the acid value was measured, and found to be 0.06. 198 kg of the mixture of fatty acid ethyl esters (acid value: 0.06) was mixed with 900 kg of a silver nitrate aqueous solution (concentration: 40%) prepared by dissolving 360 kg of silver nitrate in 540 kg of distilled water with stirring. The mixture was stirred at 10° C. for 20 minutes.

The mixture was then allowed to stand for 1 hour until the mixture was separated into two phases. The lower layer was then isolated. After adding 1000 kg of water to the isolated product, this mixture was stirred at 60° C. for 20 minutes. The mixture was then allowed to stand for 1 hour until the mixture was separated into two phases. The upper layer was isolated to obtain a concentrate of a polyunsaturated fatty acid ethyl ester. Separately, the lower layer containing silver nitrate was collected, and the free fatty acid content was measured. The lower layer containing silver nitrate was concentrated, adjusted in concentration, and again used to obtain a polyunsaturated fatty acid ethyl ester. The above operations were repeated to treat 10 batches of the above mixture of polyunsaturated fatty acid ethyl esters (acid value: 0.06). The free fatty acid content in the silver nitrate aqueous solution was 0.2 meq or less per gram of silver (see Table 5). The product thus obtained (EPA ethyl ester concentration: 81 to 85%) had a satisfactory POV, acid value, and quality such as flavor.

TABLE 5

| Batch No. | Silver salt Free fatty acid content (meq/g) | POV (meq/kg) | Acid value | Flavor | Yield (%) | EPA ethyl ester (%) | DHA ethyl ester (%) |
|---|---|---|---|---|---|---|---|
| 1 | 0.012 | 3.8 | 0.05 | Good | 86.5 | 81.7 | 2.3 |
| 2 | 0.015 | 2.3 | 0.06 | Good | 86.2 | 81.6 | 2.2 |
| 3 | 0.026 | 2.3 | 0.21 | Good | 87.8 | 81.5 | 2.1 |
| 4 | 0.025 | 2.6 | 0.09 | Good | 87.8 | 81.5 | 2.2 |
| 5 | 0.031 | 1.0 | 0.09 | Good | 87.8 | 82.3 | 2.2 |
| 6 | 0.048 | 2.1 | 0.10 | Good | 91.2 | 83.2 | 2.3 |
| 7 | 0.045 | 1.6 | 0.18 | Good | 93.5 | 83.3 | 2.1 |
| 8 | 0.048 | 1.9 | 0.14 | Good | 85.9 | 83.8 | 2.4 |
| 9 | 0.047 | 1.8 | 0.14 | Good | 83.8 | 83.7 | 2.2 |
| 10 | 0.059 | 2.2 | 0.28 | Good | 84.8 | 84.5 | 2.3 |

Example 6

A polyunsaturated fatty acid ethyl ester was obtained from a mixture of fatty acid ethyl esters by the following method.

350 kg of distilled water was added to 400 kg of silver perchlorate. The mixture was stirred to obtain a silver perchlorate aqueous solution. After adding 160 kg of a mixture of fatty acid ethyl esters (acid value: 0.06, POV: 2.7, EPA ethyl ester concentration: 47.9%, DHA ethyl ester concentration: 3.2%) to the silver perchlorate aqueous solution (750 kg), the mixture was stirred at 10° C. for 20 minutes. The mixture was then allowed to stand for 1 hour until the mixture was separated into two phases. The lower layer was then isolated. After adding 1000 kg of water to the isolated product, this mixture was stirred at 60° C. for 20 minutes. The mixture was then allowed to stand for 1 hour until the mixture was separated into two phases. The upper layer was isolated to obtain a concentrate of a polyunsaturated fatty acid ethyl ester. Separately, the lower layer containing silver perchlorate was collected, and the free fatty acid content was measured. The lower layer containing silver perchlorate was concentrated, adjusted in concentration, and again used to obtain a polyunsaturated fatty acid ethyl ester. The above operations were repeated to treat 10 batches of the mixture. The results are shown in Table 6. The free fatty acid content in the silver perchlorate aqueous solution was 0.2 meq or less per gram of silver all the time. The product thus obtained (EPA ethyl ester concentration: 82 to 85%) had a satisfactory POV, acid value, and quality such as flavor.

TABLE 6

| Batch No. | Silver salt Free fatty acid content (meq/g) | Polyunsaturated fatty acid derivative obtained |||||
|---|---|---|---|---|---|---|
| | | POV (meq/kg) | Acid value | Flavor | Yield (%) | EPA ethyl ester (%) | DHA ethyl ester (%) |
| 1  | 0.056 | 3.4 | 0.18 | Good | 72.7 | 82.6 | 8.1 |
| 2  | 0.073 | 3.1 | 0.21 | Good | 71.5 | 83.6 | 8.8 |
| 3  | 0.079 | 3.9 | 0.29 | Good | 72.9 | 84.7 | 7.9 |
| 4  | 0.082 | 4.3 | 0.25 | Good | 71.1 | 83.3 | 8.5 |
| 5  | 0.085 | 4.1 | 0.32 | Good | 69.1 | 82.1 | 9.2 |
| 6  | 0.086 | 3.9 | 0.28 | Good | 69.9 | 81.9 | 8.5 |
| 7  | 0.088 | 4.1 | 0.25 | Good | 70.3 | 83.4 | 9.3 |
| 8  | 0.092 | 3.8 | 0.18 | Good | 66.1 | 85.1 | 9.3 |
| 9  | 0.094 | 2.8 | 0.31 | Good | 67.9 | 82.8 | 10.1 |
| 10 | 0.101 | 3.8 | 0.26 | Good | 66.6 | 83.7 | 9.4 |

Reference Example 1

A polyunsaturated fatty acid ethyl ester was obtained from a mixture of fatty acid ethyl esters by the following method.

350 kg of distilled water was added to 350 kg of silver nitrate. The mixture was stirred to obtain a silver nitrate aqueous solution. After adding 150 kg of a mixture of fatty acid ethyl esters (acid value: 10.20, POV: 3.7, EPA ethyl ester concentration: 49.0%, DHA ethyl ester concentration: 8.6%) to the silver nitrate aqueous solution (700 kg), the mixture was stirred at 10° C. for 20 minutes. The mixture was then allowed to stand for 1 hour until the mixture was separated into two phases. The lower layer was then isolated. After adding 1000 kg of water to the isolated product, this mixture was stirred at 60° C. for 20 minutes. The mixture was then allowed to stand for 1 hour until the mixture was separated into two phases. The upper layer was isolated to obtain a concentrate of a polyunsaturated fatty acid ethyl ester. Separately, the lower layer containing silver nitrate was collected, and the free fatty acid content was measured. The lower layer containing silver nitrate was concentrated, adjusted in concentration, and again used to obtain a polyunsaturated fatty acid ethyl ester. The above operations were repeated to treat 3 batches of the mixture. The results are shown in Table 7. As shown in Table 7, when the acid value of the mixture of fatty acid ethyl esters before contacting the mixture with the silver nitrate aqueous solution exceeded 5, the free fatty acid content in the silver nitrate aqueous solution increased when repeatedly using the silver nitrate aqueous solution, resulting in obtaining the polyunsaturated fatty acid derivative having an increased POV and acid value and an impaired flavor.

TABLE 7

| Batch No. | Silver salt Free fatty acid content (meq/g) | Polyunsaturated fatty acid derivative obtained |||||
|---|---|---|---|---|---|---|
| | | POV (meq/kg) | Acid value | Flavor | Yield (%) | EPA ethyl ester (%) | DHA ethyl ester (%) |
| 1 | 0.068 | 2.8 | 1.40 | Good | 73.9 | 75.9 | 15.7 |
| 2 | 0.169 | 3.9 | 2.27 | Slight fishy odor | 73.2 | 75.6 | 15.9 |
| 3 | 0.319 | 5.2 | 3.58 | Strong fishy odor | 72.1 | 75.8 | 16.2 |

Comparative Example 1

A polyunsaturated fatty acid ethyl ester was obtained from a mixture of fatty acid ethyl esters by the following method.

154 kg of a mixture of fatty acid ethyl esters (acid value: 0.08, POV: 3.3, EPA ethyl ester concentration: 45.6%, DHA ethyl ester concentration: 3.8%) was added to the silver nitrate aqueous solution (free fatty acid content: 0.319 meq per gram of silver) used to treat 3 batches of the raw material in Reference Example 1. The mixture was then stirred at 10° C. for 20 minutes. The mixture was then allowed to stand for 1 hour until the mixture was separated into two phases. The lower layer was then isolated. After adding 1000 kg of water to the isolated product, this mixture was stirred at 60° C. for 20 minutes. The mixture was then allowed to stand for 1 hour until the mixture was separated into two phases. The upper layer was isolated to obtain a concentrate of a polyunsaturated fatty acid ethyl ester. Separately, the lower layer containing silver nitrate was collected, and the free fatty acid content was measured. The results are shown in Table 8. As shown in Table 8, even if the mixture of fatty acid derivatives had a low acid value before contacting the mixture with the silver salt aqueous solution, the polyunsaturated fatty acid derivative obtained by the silver complex-forming technique had unsatisfactory quality when the free fatty acid content in the silver salt aqueous solution exceeded 0.2 meq per gram of silver.

TABLE 8

| Batch No. | Silver salt Free fatty acid content (meq/g) | Polyunsaturated fatty acid derivative obtained |||||
|---|---|---|---|---|---|---|
| | | POV (meq/kg) | Acid value | Flavor | Yield (%) | EPA ethyl ester (%) | DHA ethyl ester (%) |
| 1 | 0.328 | 3.3 | 0.59 | Strong fishy odor | 73.2 | 81.9 | 7.1 |

The invention claimed is:

1. A method of obtaining a polyunsaturated fatty acid derivative comprising the steps of:
   contacting a mixture of fatty acid derivatives including a polyunsaturated fatty acid derivative with a silver salt aqueous solution to obtain the polyunsaturated fatty acid derivative;
   collecting a separated silver salt aqueous solution therefrom, and adjusting a free fatty acid content in the collected silver salt aqueous solution to 0.2 meq or less per gram of silver to obtain a collected and adjusted silver salt aqueous solution; and
   re-using the collected and adjusted silver salt aqueous solution.

2. The method according to claim 1, wherein the free fatty acid content is adjusted to 0.2 meq or less per gram of silver by contacting the collected silver salt aqueous solution with an adsorbent.

3. The method according to claim 1 or 2, wherein the mixture of fatty acid derivatives before being contacted with the silver salt aqueous solution has an acid value of 5 or less.

4. The method according to claim 1, wherein the acid value of the mixture of fatty acid derivatives before being contacted with the silver salt aqueous solution is adjusted to 5 or less by contacting the mixture with an adsorbent.

5. A method of obtaining a polyunsaturated fatty acid derivative comprising the steps of: contacting a mixture of fatty acid derivatives including a polyunsaturated fatty acid derivative with a silver salt aqueous solution comprising a silver salt and free fatty acids having a free fatty acid content of 0.2 meq or less per gram of silver, forming a water-soluble complex of a polyunsaturated fatty acid derivative and silver salt, and separating the polyunsaturated fatty acid derivative in the water-soluble complex of the polyunsaturated fatty acid derivative from the silver salt aqueous solution.

* * * * *

UNITED STATES PATENT AND TRADEMARK OFFICE
CERTIFICATE OF CORRECTION

PATENT NO. : 8,680,305 B2  Page 1 of 1
APPLICATION NO. : 13/062969
DATED : March 25, 2014
INVENTOR(S) : Sakaguchi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 283 days.

Signed and Sealed this

Twenty-ninth Day of September, 2015

Michelle K. Lee
*Director of the United States Patent and Trademark Office*